United States Patent
Scheiner

(10) Patent No.: US 8,818,508 B2
(45) Date of Patent: Aug. 26, 2014

(54) DOSING VAGAL NERVE STIMULATION THERAPY IN SYNCHRONIZATION WITH TRANSIENT EFFECTS

(75) Inventor: Avram Scheiner, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 679 days.

(21) Appl. No.: 13/046,387

(22) Filed: Mar. 11, 2011

(65) Prior Publication Data
US 2011/0224750 A1 Sep. 15, 2011

Related U.S. Application Data

(60) Provisional application No. 61/313,334, filed on Mar. 12, 2010, provisional application No. 61/330,121, filed on Apr. 30, 2010, provisional application No. 61/330,103, filed on Apr. 30, 2010.

(51) Int. Cl.
*A61N 1/365* (2006.01)
*A61N 1/36* (2006.01)

(52) U.S. Cl.
CPC .. *A61N 1/365* (2013.01); *A61N 1/36* (2013.01)
USPC .................................. 607/17; 607/2; 607/62

(58) Field of Classification Search
CPC .................................. A61N 1/36; A61N 1/365
USPC .......................................................... 607/17
See application file for complete search history.

(56) References Cited

U.S. PATENT DOCUMENTS

| | | | |
|---|---|---|---|
| 2003/0040774 A1* | 2/2003 | Terry et al. | 607/2 |
| 2004/0193231 A1* | 9/2004 | David et al. | 607/48 |
| 2007/0233194 A1* | 10/2007 | Craig | 607/2 |
| 2008/0243204 A1* | 10/2008 | Uthman et al. | 607/45 |
| 2009/0088817 A1* | 4/2009 | Starkebaum et al. | 607/40 |
| 2012/0158082 A1* | 6/2012 | Katra | 607/17 |
| 2012/0158086 A1* | 6/2012 | Katra | 607/17 |

* cited by examiner

*Primary Examiner* — Carl H Layno
*Assistant Examiner* — Jennifer Ghand
(74) *Attorney, Agent, or Firm* — Carol F. Barry

(57) ABSTRACT

The present disclosure is directed to a method of using an implantable medical device. One embodiment of the present disclosure comprises delivering electrical stimulation proximate nerve tissue of a patient during a transient physiological effect period separated by a recovery period. The transient physiological effect period is when electrical stimulation has an increased level of efficacy and the recovery period is when additional electrical stimulation does not provide a beneficial physiological effect to the patient.

22 Claims, 9 Drawing Sheets

DOSING VAGAL NERVE STIMULATION THERAPY IN SYNCHRONIZATION WITH TRANSIENT EFFECTS

CROSS-REFERENCE TO RELATED APPLICATIONS

This application claims the benefit of U.S. Provisional Application No. 61/313,334, filed on Mar. 12, 2010, entitled "DOSING VAGAL NERVE STIMULATION THERAPY IN SYNCHRONIZATION WITH TRANSIENT EFFECTS", U.S. Provisional Application No. 61/330,121, filed Apr. 30, 2010, entitled "DOSING VAGAL NERVE STIMULATION THERAPY IN SYNCHRONIZATION WITH TRANSIENT EFFECTS", and U.S. Provisional Application No. 61/330,103, filed Apr. 30, 2010, entitled "CONTROLLING NERVE STIMULATION THERAPY IN SYNCHRONIZATION WITH TRANSIENT EFFECTS. The disclosure of the above application is incorporated herein by reference in its entirety.

TECHNICAL FIELD

The present disclosure relates to medical devices and, more particularly, medical devices that deliver electrical stimulation therapy.

BACKGROUND

A wide variety of implantable medical devices ("IMD") that deliver therapy to or monitor a physiologic condition of a patient have been clinically implanted or proposed for clinical implantation in patients. Such devices may deliver therapy or monitor the heart, muscle, nerve, the brain, the stomach or other organs or tissues. In some cases, IMD's deliver electrical stimulation therapy and/or monitor physiological signals via one or more electrodes or sensor elements, at least some of which may be included as part of one or more elongated implantable medical leads. Implantable medical leads may be configured to allow electrodes or sensors to be positioned at desired locations for delivery of stimulation or sensing electrical activity or other physiological parameters. For example, electrodes or sensors may be located at a distal portion of the lead. A proximal portion of the lead is coupled to an IMD housing, which contains electronic circuitry such as stimulation generation and/or sensing circuitry. In some cases, electrodes or sensors are positioned on an IMD housing as an alternative or in addition to electrodes or sensors deployed on one or more leads.

One example IMD is an electrical stimulation device directed to nerve tissue stimulation, which is sometimes referred to as an implantable nerve stimulator or implantable neurostimulator ("INS"). One particular application of nerve tissue stimulation is vagal nerve stimulation. Vagal nerve stimulation may provide therapeutic effects for heart failure, as well as other conditions including, e.g., depression, epilepsy and various digestion conditions. It is desirable to develop new techniques to control electrical stimulation of nerve tissue.

SUMMARY

In general, one or more embodiments disclosed herein are directed to lowering of a heart rate of a patient. One embodiment of the present disclosure comprises delivering electrical stimulation proximate nerve tissue of a patient during a transient physiological effect period separated by a recovery period. The transient physiological effect period is when electrical stimulation has an increased level of efficacy and the recovery period is when additional electrical stimulation does not provide a beneficial physiological effect to the patient.

The details of one or more examples according to this disclosure are set forth in the accompanying drawings and the description below. Other features, objects, and advantages will be apparent from the description and drawings, and from the claims.

DETAILED DESCRIPTION

Figure 1A:
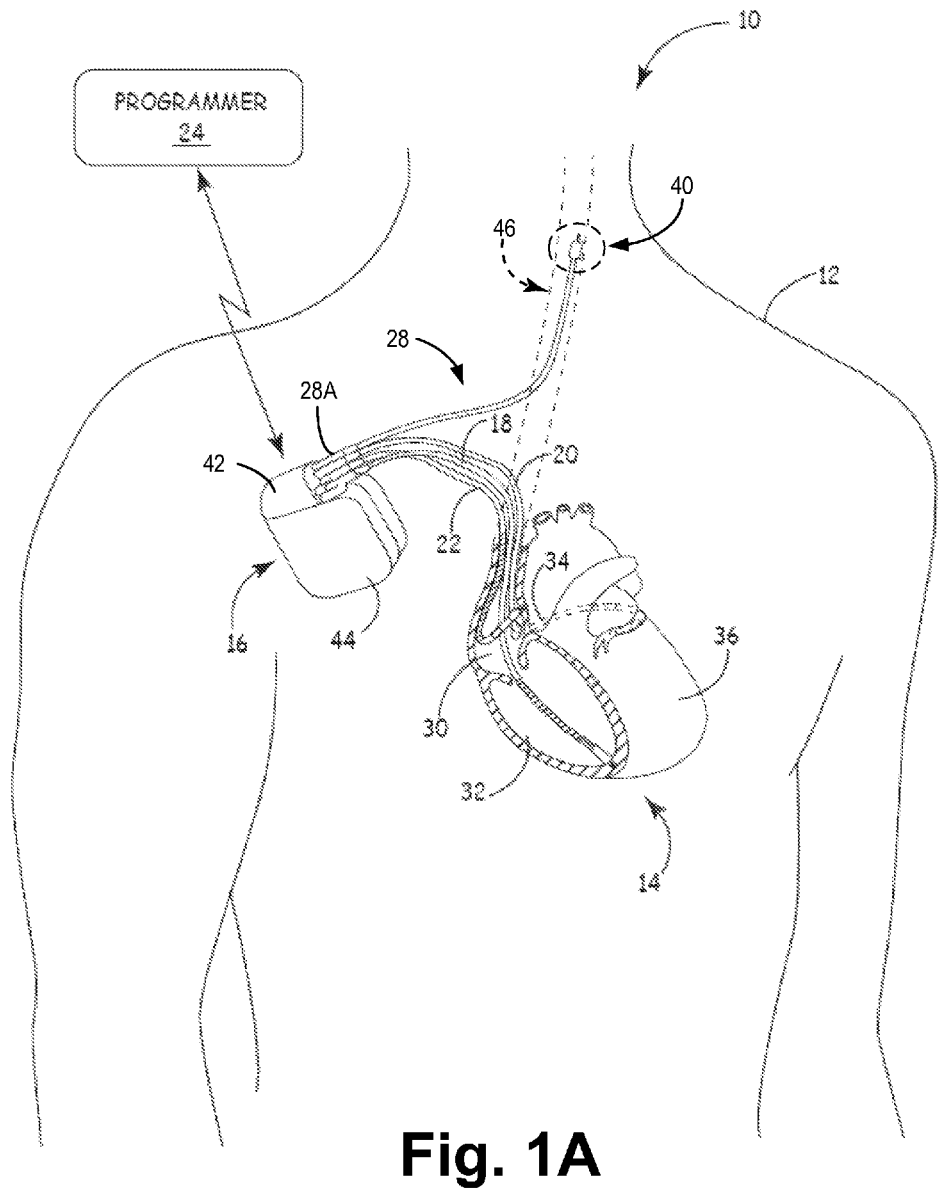
FIG. 1A is a conceptual diagram illustrating an example therapy system including an implantable medical device (IMD) that delivers cardiac and nerve tissue stimulation to a patient.

In general, this disclosure is directed toward techniques that involve dosing vagal nerve stimulation therapy (VNS) in synchronization with transient effects.

In one or more embodiments, a medical electrical lead is placed proximate nerve tissue within a patient for electrical stimulation of the tissue. Specific types of electrical stimulation therapies for treating such conditions include, e.g., cardiac pacing, neurostimulation, muscle stimulation, or the like.

The techniques disclosed herein are described generally in the context of stimulation of one of the vagus nerves on the vagal nerve trunk in the neck of a human patient. Vagal nerve stimulation is useful in treating various conditions including, e.g., heart failure. The methods and systems disclosed may also be applicable to stimulation and treatment of other nerve tissues that are located in diverse locations.

For example, the disclosed techniques may be used in the stimulation of a hypoglossal nerve. In other examples, a nerve plexus that forms a node of intersecting nerves including, e.g., the cervical, brachial, lumbar, sacral, or solar plexus may be stimulated using methods and systems according to this disclosure. Additionally, the techniques may be used for stimulation of nerve ganglia including, e.g., one or more ganglia of a nerve plexus.

As an additional example, the techniques disclosed herein may be used in the stimulation of vascular baroreceptors including, e.g., carotid baroreceptors. Baroreceptors are sensors located in blood vessels that detect the pressure of blood flowing therethrough, and can send messages to the central nervous system to increase or decrease total peripheral resistance and cardiac output. The receptors function by detecting the amount a blood vessel wall stretches, and sending a signal to the nervous system in response to the detected expansion of the vessel. Baroreceptors act as part of a negative feedback system called the baroreflex that returns blood pressure to a normal level as soon as there is a deviation from a typical pressure, such as, e.g., the mean arterial blood pressure.

As used herein, the term sheath of tissue generally refers to constraining connective tissue that holds together different biological structures within the body of a patient (e.g., a common carotid sheath). Intra or transvascular lead placement proximate the target nerve tissue, on the other hand, generally requires minimally invasive surgical techniques because the leads may be guided to the site through a blood vessel, e.g., a vein or artery, that may be readily accessible, e.g., transcutaneously through a small incision. Intra and transvascular lead placement techniques described herein may facilitate placing the distal end of the lead in close proximity of the target nerve tissue, the relative position of which with respect to an adjacent blood vessel may vary from patient-to-patient. Additionally, guided transvascular lead placement as described herein may avoid safety risks of such procedures including, e.g., piercing adjacent vessels, such as an artery.

Transvascular techniques generally include improving lead placement by locating target nerve tissue with a sensor including, e.g., an IVUS imaging system, through a blood vessel adjacent the target tissue. An example of transvascular lead placement and technique may be seen with respect to U.S. pat. application Ser. No. 12/433,809 filed Apr. 30, 2009, and assigned to the assignee of the present invention, the disclosure of which is incorporated by reference in its entirety herein. After a placement location is determined, one or more leads including one or more electrodes may be deployed through the vessel wall and anchored to the vessel wall or other tissue near the target nerve tissue.

FIG. 1A is a conceptual diagram illustrating an example therapy system 10 that provides cardiac rhythm therapy and nerve tissue stimulation therapy to patient 12. Therapy system 10 includes implantable medical device (IMD) 16, which is connected (or "coupled") to leads 18, 20, 22, 28, and programmer 24. IMD 16 may be subcutaneously or submuscularly implanted in the body of a patient 12 (e.g., in a chest cavity, lower back, lower abdomen, or buttocks of patient 12).

IMD 16 may include a cardiac therapy module (not shown in FIG. 1A) and a neurostimulation module (not shown in FIG. 1A) enclosed within outer housing 44. The cardiac therapy module may generate and deliver cardiac rhythm management therapy to heart 14 of patient 12, and may include, for example, an implantable pacemaker, cardioverter, and/or defibrillator that provide therapy to heart 14 of patient 12 via electrodes coupled to one or more of leads 18, 20, and 22. In some examples, the cardiac therapy module may deliver pacing pulses, but not cardioversion or defibrillation pulses, while in other examples, the cardiac therapy module may deliver cardioversion or defibrillation pulses, but not pacing pulses. In addition, in further examples, cardiac therapy module may deliver pacing, cardioversion, and defibrillation pulses. IMD 16 may deliver pacing that includes one or both of anti-tachycardia pacing (ATP) and cardiac resynchronization therapy (CRT).

The neurostimulation module of IMD 16 may include a signal generator that generates and delivers electrical stimulation to a tissue site of patient 12, e.g., tissue proximate a vagus nerve or other target nerve tissue of patient 12. In some examples, the tissue site may include a peripheral nerve. The tissue site may include a nerve plexus that forms a node of intersecting nerves including, e.g., the cervical, brachial, lumbar, sacral, or solar plexus. Additionally, the techniques may be used for stimulation of nerve ganglia including, e.g., one or more ganglia of a nerve plexus. As an additional example, the techniques disclosed herein may be used in the treatment of vascular baroreceptors including, e.g., carotid baroreceptors. In the example shown in FIG. 1A, electrodes of lead 28 are positioned to deliver electrical stimulation to a target tissue site 40 proximate a vagus nerve of patient 12. The vagus nerve is primarily referred to herein as an exemplary target nerve for neurostimulation therapy.

In some examples, delivery of electrical stimulation to a nerve tissue site may provide cardiac benefits to patient 12. For example, delivery of electrical stimulation to a peripheral nerve tissue site by IMD 16 may help treat heart failure. In addition, delivery of electrical stimulation to a nerve of patient 12 may help reduce or eliminate cardiovascular conditions such as bradycardia, tachycardia, unhealthy cardiac contractions, ischemia, inefficient heart pumping, inefficient collateral circulation of heart 14 or cardiac muscle trauma. In addition, delivery of electrical stimulation to a nerve may complement antitachycardia pacing or provide back-up therapy to cardiac therapy delivered by IMD 16. In some examples, IMD 16 may deliver electrical stimulation therapy to a nerve of patient 12 via a lead implanted within vasculature (e.g., a blood vessel) of patient 12. In other examples, stimulation may be delivered by IMD 16 via a lead located in extravascular tissue, e.g., when lead 28 is not implanted within vasculature, such as within a vein or artery. Additional examples include transvascular placement of a lead from within a blood vessel of patient 12 adjacent the target tissue site, through the wall of the blood vessel, and into an extravascular space, where the target nerve tissue may be located.

In the example shown in FIG. 1A, the neurostimulation therapy module of IMD 16 delivers electrical stimulation therapy to a nerve of patient 12 via a lead implanted within vasculature (e.g., a blood vessel) of patient 12. In particular, lead 28 is implanted such that electrodes of lead 28 are positioned within jugular vein 46 proximate the vagus nerve (not shown). Stimulation of a parasympathetic nerve of patient 12 may help slow intrinsic rhythms of heart 14, which may complement antitachyarrhythmia therapy (e.g., antitachycardia pacing, cardioversion or defibrillation) delivered by IMD 16. In this way, neurostimulation therapy may help control a heart rate of patient 12 or otherwise control cardiac function.

In other examples, electrodes of lead 28 may be positioned to deliver electrical stimulation to any other suitable nerve (e.g., a peripheral nerve) or nerve tissue in patient 12. In some examples, the neurostimulation module of IMD 16 may deliver electrical stimulation to other sympathetic or parasympathetic nerves, baroreceptors, hypoglossal nerve, carotid sinus, or a cardiac branch of the vagal trunk of patient 12 in order to facilitate or compliment the delivery of therapy by the cardiac therapy module of IMD 16.

In FIG. 1A, leads 18, 20, and 22 extend into the heart 14 of patient 12 to sense electrical activity (electrical cardiac signals) of heart 14 and/or deliver electrical stimulation (cardiac therapy) to heart 14. In particular, right ventricular (RV) lead 18 extends through one or more veins (not shown), superior vena cava (not shown), and right atrium 30, and into right ventricle 32. Left ventricular (LV) coronary sinus lead 20 extends through one or more veins, the vena cava, right atrium 30, and into coronary sinus 34 to a region adjacent to the free wall of left ventricle 36 of heart 14. Right atrial (RA) lead 22 extends through one or more veins and the vena cava, and into right atrium 30 of heart 14. In other examples, IMD 16 is additionally or alternatively coupled to extravascular, e.g., epicardial or subcutaneous electrodes, via leads for cardiac sensing and/or stimulation.

The cardiac therapy module may sense electrical signals attendant to the depolarization and repolarization of heart 14 via electrodes (not shown in FIG. 1A) coupled to at least one of the leads 18, 20, 22. These electrical signals within heart 14 may also be referred to as cardiac signals or electrical cardiac signals. In some examples, the cardiac therapy module provides pacing pulses to heart 14 based on the electrical cardiac signals sensed within heart 14. The configurations of electrodes used by the cardiac therapy module for sensing and pacing may be unipolar or bipolar. The cardiac therapy module may also provide defibrillation therapy and/or cardioversion therapy via electrodes located on at least one of the leads 18, 20, 22 and one or more electrodes on housing 44 of IMD 16. IMD 16 may detect arrhythmia of heart 14, such as fibrillation of ventricles 32 and 36, and deliver defibrillation therapy to heart 14 in the form of electrical pulses via one or more of leads 18, 20, and 22. In some examples, the cardiac therapy module may be programmed to deliver a progression of therapies, e.g., pulses with increasing energy levels, until a fibrillation of heart 14 is stopped. IMD 16 detects fibrillation employing one or more fibrillation detection techniques known in the art.

The neurostimulation therapy module of IMD 16 may provide a programmable stimulation signal (e.g., in the form of electrical pulses or a continuous signal) that is delivered to target stimulation site 40 by implantable medical lead 28, and more particularly, via one or more stimulation electrodes carried by lead 28. Proximal end 28A of lead 28 may be both electrically and mechanically coupled to connector 42 of IMD 16 either directly or indirectly (e.g., via a lead extension). In particular, conductors disposed in the lead body of lead 28 may electrically connect stimulation electrodes (and sense electrodes, if present) of lead 28 to IMD 16. In some examples, the neurostimulation therapy module of IMD 16 may be electrically coupled to more than one lead directly or indirectly (e.g., via a lead extension).

In the example of FIG. 1A, one or more electrodes of lead 28 are intravascularly implanted in patient 12 proximate to target tissue stimulation site 40, e.g., proximate to a vagus nerve (not shown). In particular, one or more neurostimulation electrodes of lead 28 are implanted within jugular vein 46. Generally speaking, implanting lead 28 near the vagus nerve of patient 12 may be useful for delivering neurostimulation therapy to the vagus nerve without requiring lead 28 to be subcutaneously implanted in patient 12. Implanting lead 28 intravascularly within jugular vein 46 may thereby be useful for reducing trauma to patient 12, e.g., because lead 28 is not tunneled through subcutaneous tissue from IMD 16 to target site 40. Lead 28 may be extravascularly or transvascularly placed proximate target tissue stimulation site 40, e.g., proximate a vagus nerve of patient 12.

The distal portion of lead 28 may include one or more electrodes (not shown) for delivering neurostimulation to target stimulation site 40. Various electrode configurations of lead 28 are described in further detail with respect to FIGS. 2 and 3. In some examples, lead 28 may also carry sense electrodes (not shown) to permit IMD 16 to sense electrical signals, such as electrical cardiac signals or electrical nerve signals from the vagus nerve or other nerve tissue at which therapy is directed. Lead 28 may also carry one or more sensors including, e.g., sense electrodes, pressure sensors, ultrasound sensors, motion sensors, acoustic sensors (heart rate), optical sensors, blood oxygen sensors, posture state sensors, respiration sensors, venous biomarker sensors, temperature sensors or other devices that may detect physiological signals of patient 12 indicative of the efficacy of neurostimulation therapy delivered to the patient by stimulation electrodes.

In some examples, IMD 16 may deliver an electrical stimulation signal via one or more of the electrodes of lead 28, and analyze a physiological signal to detect a response to the stimulation signal. In one such example, IMD 16 analyzes an electrical nerve signal to detect a response to the stimulation signal. The characteristic of the electrical nerve signal that indicates the desired response to the delivery of the electrical stimulation signal by the neurostimulation therapy module of IMD 16 may be, for example, an amplitude or frequency of the electrical signal. The target characteristic of the electrical nerve signal may be determined by a clinician at any suitable time when lead 28 is known to be in the desired location within patient 12, e.g., immediately after lead 28 is implanted within patient 12.

The electrical nerve signal may be an electrical signal generated by a nerve, such as the target nerve for the neurostimulation therapy or a branch thereof, in response to an electrical stimulation signal delivered by the electrodes of lead 28. The response to the electrical stimulation signal may indicate, for example, whether the neurostimulation signal captured the nerve, and, therefore, is within a desired distance of the nerve. In the example shown in FIG. 1A, the target nerve is a vagus nerve, however, other types of nerves are contemplated for the neurostimulation therapy. The electrical nerve signal may be sensed between two or more electrodes of lead 28. IMD 16 may analyze the electrical nerve signal for a response, for example, by measuring an amplitude of the electrical nerve signal and comparing the determined value to a threshold value. In this case, the electrical nerve signal may have a baseline amplitude value and a response to the stimulation signal may be characterized by a spike in amplitude. The nerve response may be characterized by an amplitude or other characteristics of a sensed electrical signal.

Sensed physiological signals may be used to determine the efficacy of neurostimulation delivered by electrodes on lead 28 to target nerve tissue. In some examples, lead 28 may be intra, extra, or transvascularly placed proximate the nerve tissue and electrodes on lead 28 may deliver test stimulation pulses to the nerve tissue in order to test the placement of lead 28 within patient 12 relative to the nerve tissue. Various physiological signals may be observed to measure the efficacy of the test stimulation, and thereby the need to reposition lead 28 relative the target nerve tissue. In some examples, test treatment efficacy may be indicated by, e.g., ECG, heart rate, blood pressure, blood flow, blood oxygen content, blood biomarker content, cardiac output, and/or breathing, of patient 12. Additionally, T-wave morphology, heart rate variability, contractility, and atrioventricular (AV) intervals may be observed as an indication of test treatment efficacy. These and other physiological signals may be detected in a variety of ways including sensing the signals using sense electrodes, pressure sensors, ultrasound sensors, motion sensors or other devices. In other examples, physiological reactions of patient 12 may be observed or measured by, e.g., a clinician.

In the case one or more sensors are employed to detect physiological signals of patient 12, such devices may be arranged in a variety of locations depending on device configuration and the particular signal being detected. For example, the efficacy of electrical stimulation of a vagus nerve may be measured by an accelerometer arranged in the neck of patient 12 that determines if stimulation of neck muscles or the phrenic nerve is occurring with or instead of stimulation of a vagus nerve. In another example, a pressure sensor arranged coincident with or connected to lead 28 may measure blood pressure by detecting the pressure within a vessel in which lead 28 is placed. A pressure sensor, or other type of physiological feedback sensor, may also, in some examples, be connected to a delivery catheter configured to place lead 28 within patient 12. In still another example, a cardiac therapy module included in IMD 16 may employ one or more electrodes arranged on or within heart 14 of patient 12 to, e.g., to monitor electrical activity of heart 14 via an electrogram (EGM) or electrocardiogram (ECG) signal. In other examples, venous biomarker sensors configured to sense, e.g., inflammation markers or catecholamines may be used to measure the effect of the stimulation and provide feedback to IMD 16.

Figure 1B:
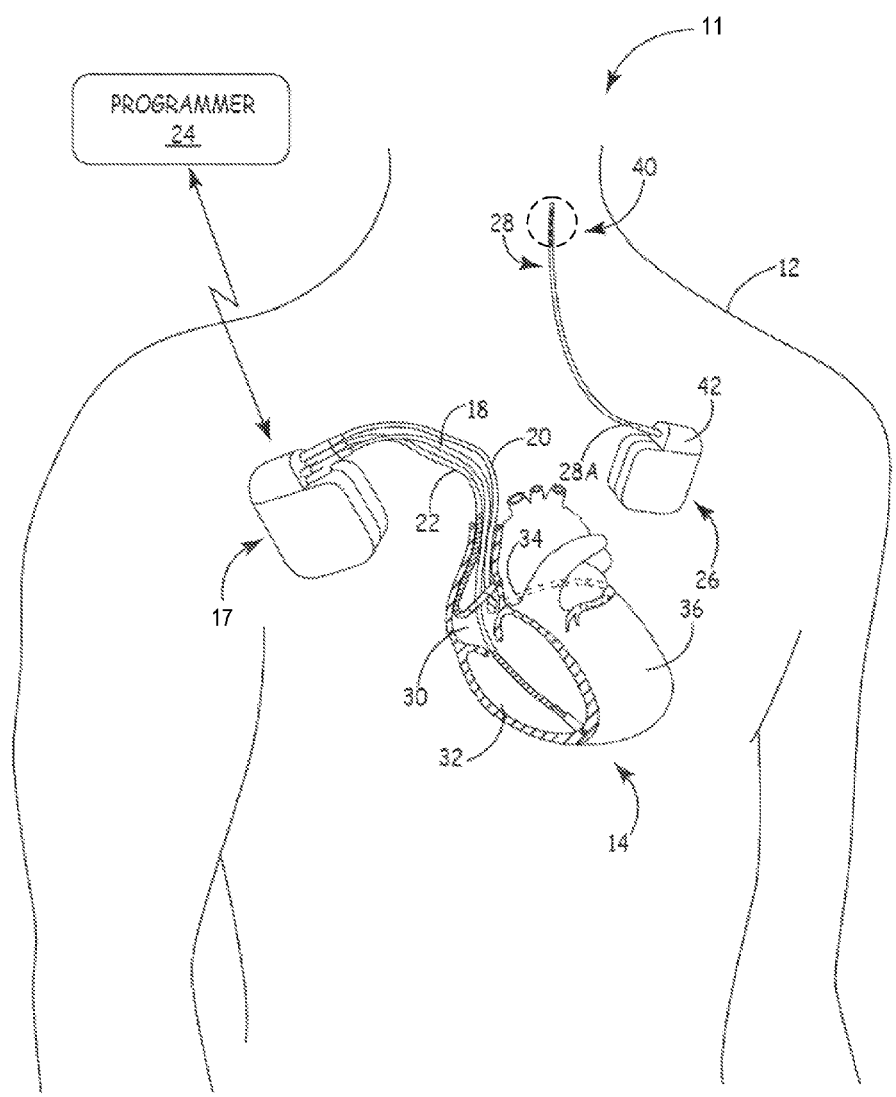
FIG. 1B is a conceptual diagram illustrating an example therapy system including an implantable cardiac device (ICD) and an implantable neurostimulator (INS).

The extra, intra, and transvascular lead placement techniques can be applicable for implantation of a variety of implantable therapy systems including, e.g., system 10 of FIG. 1A, as well as systems that do not deliver cardiac stimulation and/or provide cardiac sensing, or, as with the example of FIG. 1B, deliver cardiac therapy using a device that is separate from and in addition to an implantable neurostimulator.

As illustrated in FIG. 1A, system 10 may include a programmer 24. IMD 16 may transmit information to and receive information from programmer 24 related to the operation of IMD 16 and/or the delivery of therapy by IMD 16 to patient 12. Upon receiving the information, programmer 24 may upload the received information to a remote server, from which a clinician may access the data (such as a remote server of the CareLink Network available from Medtronic, Inc. of Minneapolis, Minn.). A clinician may also access the information directly by interacting with programmer 24. Furthermore, the clinician may program various aspects of the operation of IMD 16 remotely by accessing a remote server that communicates with IMD 16 via a network and programmer 24, or locally program IMD 16 by physically interacting with programmer. In some examples, the clinician may interact with programmer 24 to, e.g., program select values for operational parameters of IMD 16.

In some examples, programmer 24 may be a handheld computing device or a computer workstation. The user may use programmer 24 to program aspects of the neurostimulation module. The therapy parameters for the neurostimulation module of IMD 16 may include an electrode combination for delivering neurostimulation signals, as well as an amplitude, which may be a current or voltage amplitude, and, if the neurostimulation module delivers electrical pulses, a pulse width, and a pulse rate for stimulation signals to be delivered to patient 12. The electrode combination may include a selected subset of one or more electrodes located on implantable lead 28 coupled to IMD 16 and/or a housing of IMD 16. The electrode combination may also refer to the polarities of the electrodes in the selected subset. By selecting particular electrode combinations, a clinician may target particular anatomic structures within patient 12. In addition, by selecting values for amplitude, pulse width, and pulse rate, the physician can attempt to generate an efficacious therapy for patient 12 that is delivered via the selected electrode subset.

As another example, programmer 24 may be used by a user, e.g., a clinician while a medical lead is placed within patient in accordance with this disclosure to retrieve or view sensor feedback during the implantation of the lead. In one example, a physician uses programmer 24 to retrieve and/or view physiological signals sensed by one or more sensors in response to test electrical stimulation pulses delivered to patient 12 during the placement of lead 12 adjacent a vagus nerve. In this manner, the physician employs programmer 24 to determine the efficacy of the test stimulation delivered by lead 28, and thereby the position of lead 28 relative to the vagus nerve. In another example, the physician may also use programmer 24 to view an imaging field produced by an IVUS imaging system connected to a delivery catheter used to place lead 28, and electrodes connected thereto intra or transvascularly within patient 12. In this manner, the physician may employ programmer 24 to view, in real time, the placement of lead 28 within patient 12 relative to target nerve tissue and a blood vessel in which or through which the lead is placed.

Programmer 24 may communicate with IMD 16 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

FIG. 1B is a conceptual diagram illustrating another example therapy system 11 that includes separate implantable cardiac device (ICD) 17 and implantable electrical stimulator 26. ICD 17 is connected to leads 18, 20, and 22, and programmer 24, while electrical stimulator 26 is coupled to lead 28 and may be communicatively connected to both ICD 17 and programmer 24. ICD 17 may be, for example, a device that provides cardiac rhythm management therapy to heart 14, and may include, for example, an implantable pacemaker, cardioverter, and/or defibrillator, as described above with reference to IMD 16.

In some examples, ICD 17 may, in addition to or instead of delivering cardiac rhythm management therapy to heart 14, sense electrical cardiac signals of heart 14 and/or other physiological parameters of patient 12 (e.g., blood oxygen saturation, blood pressure, temperature, heart rate, respiratory rate, and the like), and store the electrical cardiac signals and/or other physiological parameters of patient 12 for later analysis by a clinician. In such examples, ICD 17 may be referred to as a patient monitoring device. Examples of patient monitoring devices include, but are not limited to, the Reveal Plus Insertable Loop Recorder, which is available from Medtronic, Inc. of Minneapolis, Minn. For ease of description, ICD 17 will be referred to herein as a cardiac rhythm management therapy delivery device.

Therapy system 11 also includes implantable electrical stimulator 26, which is coupled to lead 28. Electrical stimulator 26 may also be referred to as an implantable neurostimulator ("INS") 26. INS 26 may be any suitable implantable medical device (IMD) that includes a signal generator that generates electrical stimulation signals that may be delivered via one or more electrodes on lead 28 to a nerve tissue site of patient 12, e.g., tissue proximate a vagus nerve.

In the example shown in FIG. 1B, electrodes of lead 28 are positioned outside the vasculature of patient 12 to deliver electrical stimulation to a vagus nerve (not shown) of patient 12. As described above, in other examples, stimulation may be delivered to a nerve tissue site via electrodes of an intravascular lead that is implanted within vasculature. In still other examples, stimulation may be delivered to a nerve tissue site within patient 12 via electrodes of a transvascular lead that is guided proximate the target tissue site intravascularly, i.e., through a vein, artery, or other blood vessel and then pierces a wall of the vessel to be arranged adjacent the target tissue outside of the blood vessel.

In the example shown in FIG. 1B, the components of ICD 17 and INS 26 are enclosed in separate housings, such that ICD 17 and INS 26 are physically separate devices. In contrast to the example of FIG. 1A in which the functionality of ICD 17 and INS 26 are be performed by IMD 16 that includes both a cardiac therapy module and an electrical stimulation therapy module. In applications in which cardiac and neurostimulation therapy operate cooperatively or sensing feedback is provided from heart 14 or a nerve tissue site within patient 12, ICD 17 and INS 26 of FIG. 1B may communicate with one another via one or more wireless communication techniques instead of being directly linked within the same device housing as in IMD 16 of therapy system 10 shown in FIG. 1A. For example, INS 26 may include one or more sensors that analyze an electrical nerve signal to detect a response to the stimulation signal delivered by ICD 17 and/or INS 26 to patient 12. ICD 17 and INS 26 may communicate wirelessly using, e.g., low frequency or radiofrequency (RF) telemetry.

Figure 2:
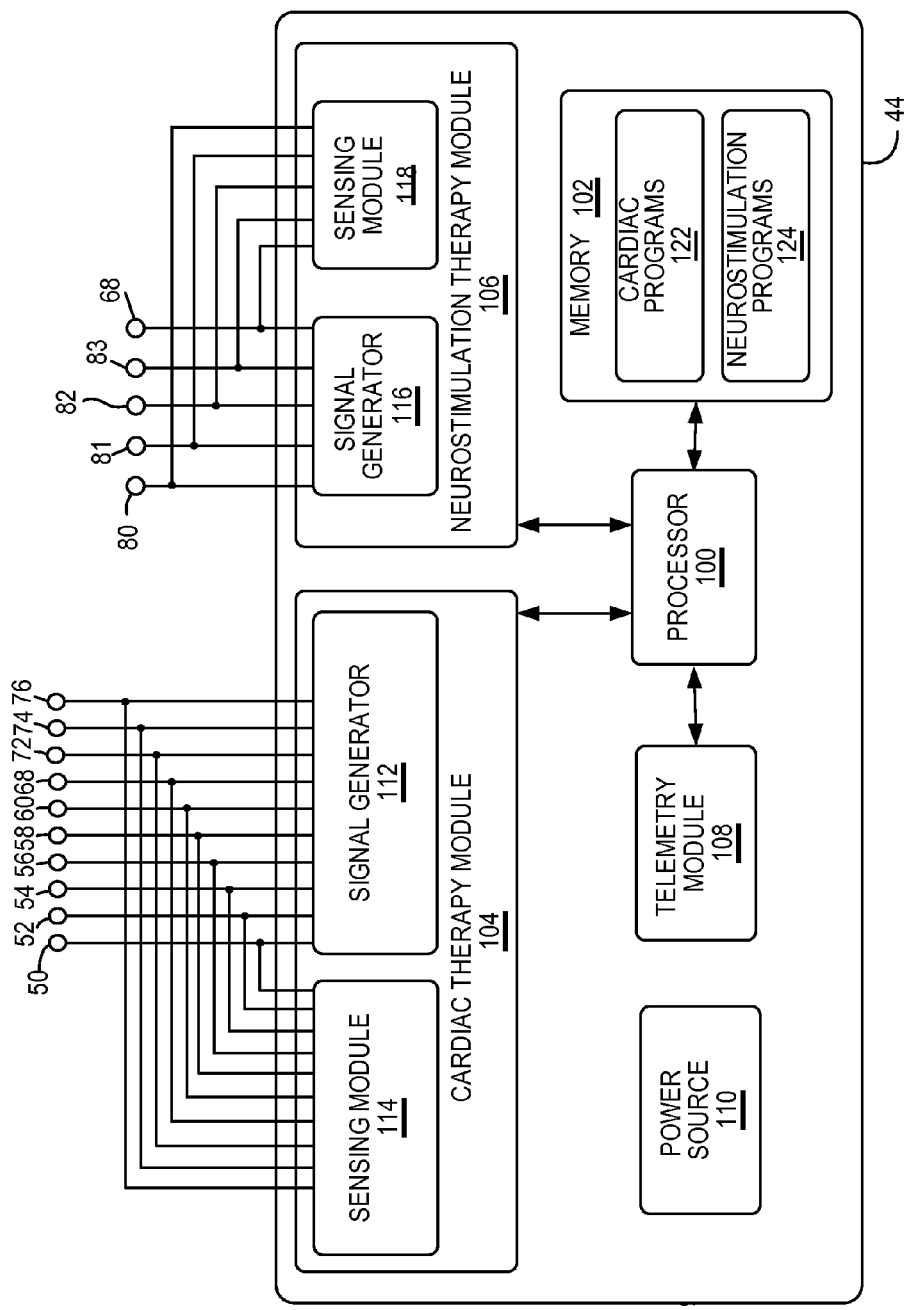
FIG. 2 is a functional block diagram of the IMD of FIG. 1A.

FIG. 2 is a functional block diagram of an example configuration of IMD 16 of FIG. 1A, which includes processor 100, memory 102, cardiac therapy module 104, neurostimulation therapy module 106, telemetry module 108, and power source 110. Cardiac therapy module 104 includes signal generator 112 and sensing module 114. Neurostimulation therapy module 106 includes signal generator 116 and sensing module 118. The components of IMD 16 shown in FIG. 2 may be substantially enclosed within a common, hermetically sealed outer housing 44 of IMD 16. In other examples including the example shown in FIG. 1B, components for carrying out the functions of cardiac therapy module 104 and neurostimulation therapy module 106 may be arranged in separate communicatively connected devices. Although cardiac therapy module 104 and neurostimulation therapy module 106 are illustrated as separate modules in FIG. 4, in some examples, cardiac therapy module 104 and neurostimulation module 106 and their respective components may share circuitry. For example, signal generators 112 and 116 may share common circuitry, e.g., a stimulation engine, charging circuitry, capacitors, and the like. Additionally, in some examples in which cardiac therapy module 104 and neurostimulation module 106 deliver stimulation in alternation, cardiac therapy module 104 and neurostimulation module 106 may share some or all stimulation generation circuitry. Similarly, in some examples, sensing modules 114 and 118 may also share common circuitry, such as an analog-to-digital converter and the like.

Memory 102 includes computer-readable instructions that, when executed by processor 100, cause IMD 16 and processor 100 to perform various functions attributed to IMD 16 and processor 100 herein. In FIG. 2, memory 102 includes cardiac programs 122 that cardiac therapy module 104 uses for generating cardiac rhythm therapy for delivery to heart 14, and neurostimulation programs 124 that neurostimulation module 106 uses for generating neurostimulation therapy for delivery to target tissue site 40. Memory 102 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 100 may include any one or more of a microprocessor, a controller, a digital signal processor (DSP), an application specific integrated circuit (ASIC), a field-programmable gate array (FPGA), or equivalent discrete or integrated logic circuitry. In some examples, processor 100 may include multiple components, such as any combination of one or more microprocessors, one or more controllers, one or more DSPs, one or more ASICs, or one or more FPGAs, as well as other discrete or integrated logic circuitry. The functions attributed to processor 100 herein may be embodied as software, firmware, hardware or any combination thereof. Processor 100 may control cardiac therapy module 104 to deliver stimulation therapy according to a selected one or more of cardiac programs 122 stored in memory 102. In addition, processor 100 may control neurostimulation module 106 to delivering stimulation therapy according to a selected one or more of neurostimulation programs 124 stored in memory 102. Specifically, processor 100 may control cardiac therapy module 104 and/or neurostimulation module 106 to deliver electrical signals via electrode combinations with amplitudes, frequency, electrode polarities, and, in the case of stimulation pulses, pulse widths specified by the selected one or more cardiac and neurostimulation therapy programs 122, 124, respectively.

In the example shown in FIG. 2, cardiac therapy module 104 is electrically connected to electrodes 50, 52, 54, 56, 58, 60, 72, 74, and 76 of leads 18, 20, and 22 and housing electrode 68, and neurostimulation module 106 is electrically connected to electrodes 80-83 of lead 28 and housing electrode 68. In other examples, cardiac therapy module 104 and neurostimulation module 106 may be coupled to any suitable number of electrodes, which may comprise a greater number of electrodes or a fewer number of electrodes than that shown in the example of FIG. 2.

Cardiac therapy module 104 is configured to generate and deliver cardiac rhythm therapy to heart 14. For example, signal generator 112 of cardiac therapy module 104 may generate and deliver cardioversion or defibrillation shocks and/or pacing pulses to heart 14 via a selected combination of electrodes 50, 52, 54, 56, 58, 60, 72, 74, and 76 and housing electrode 68. Signal generator 112 of cardiac therapy module 104 is electrically coupled to electrodes 50, 52, 54, 56, 58, 60, 72, 74, and 76, e.g., via conductors of the respective lead 18, 20, 22, or, in the case of housing electrode 68, via an electrical conductor disposed within housing 44 of IMD 16.

Sensing module 114 monitors signals from at least one of electrodes 50, 52, 54, 56, 58, 60, 72, 74, and 76 in order to monitor electrical activity of heart 14, e.g., via an EGM or ECG signal. Sensing module 114 may also include a switching module (not shown in FIG. 4) to select a particular subset of available electrodes to sense heart activity. In this manner, sensing module 114 may detect R-waves, P-waves, or other cardiac electrical activity, and provide indications of their occurrence to processor 100. In some examples, processor may analyze a digitized the EGM or ECG to detect these or other morphological features of the EGM or ECG, to determine heart rates or intervals (e.g., R-R intervals) or sizes of features such as T-waves or QRS complexes, or provide any other known cardiac sensing and monitoring functionality.

Neurostimulation module 106 is configured to generate and deliver electrical stimulation therapy to a target site within patient 12 proximate nerve tissue, e.g., in order to modulate an autonomic nervous system or vascular tone. Example stimulation sites for neurostimulation module 106 include, but are not limited to, tissue proximate a vagus nerve or branches of a vagus nerve of patient 12. For example, signal generator 116 may generate stimulation signals that are delivered to a tissue site proximate a vagus nerve via a selected combination of electrodes 80-83 of lead 28 and/or housing electrode 68. The stimulation signals may be pulses as primarily described herein, or continuous time signals, such as sine waves. Another exemplary stimulation site is baroreceptors of the carotid artery.

Signal generator 116 may be a single or multi-channel signal generator. In particular, signal generator 116 may be capable of delivering, a single stimulation pulse, multiple stimulation pulses, or a continuous signal at a given time via a single electrode combination or multiple stimulation pulses at a given time via multiple electrode combinations. In some examples, however, neurostimulation therapy module 106 may be configured to deliver multiple channels on a time-interleaved basis. In this case, neurostimulation therapy module 106 may include a switching module (not shown) that serves to time division multiplex the output of the signal generator across different electrode combinations at different times to deliver multiple programs or channels of stimulation energy to patient 12.

Sensing module 118 of neurostimulation module 106 monitors signals from at least one of electrodes 80-83 of lead 28 and housing electrode 68 in order to monitor electrical activity of the target nerve tissue, e.g. nerve signals of a vagus nerve. For example, the amount of afferent and efferent signals of nerve fibers can be monitored. In one such example, the nerve signals of the left vagus nerve of patient 12 can be compared to the right vagus nerve and therapy may be delivered by neurostimulation module 106 and/or cardiac therapy module 104 as commanded by processor 100 based at least in part upon this comparison of sensed nerve tissue traffic. Conversely, therapy may be delivered to a vagus nerve (e.g. left or right, or both) by one or more of electrodes 80-83 and sensing module 118 of neurostimulation module 106 and/or sensing module 114 of cardiac therapy module 104 as commanded by processor 100 may monitor afferent and efferent signals of vagal nerve fibers to measure the efficacy of the therapy.

Telemetry module 108 includes any suitable hardware, firmware, software or any combination thereof for communicating with another device, such as programmer 24 (FIG. 1). Under the control of processor 100, telemetry module 108 may receive downlink telemetry from and send uplink telemetry to programmer 24 with the aid of an antenna, which may be internal and/or external. Processor 100 may provide the data to be uplinked to programmer 24 and the control signals for the telemetry circuit within telemetry module 108, e.g., via an address/data bus. In some examples, telemetry module 108 may provide received data to processor 100 via a multiplexer.

The various components of IMD 16 are coupled to power source 100, which may include a rechargeable or non-rechargeable battery or a supercapacitor. A non-rechargeable battery may be selected to last for several years, while a rechargeable battery may be inductively charged from an external device, e.g., on a daily or weekly basis. Power source 100 may also include an external or a subcutaneously implanted RF transmitter that is configured to deliver power via radio frequency pulses to a receiver arranged with IMD 16 or one of the leads and/or electrodes of cardiac therapy module 104 and neurostimulation therapy module 106. In other examples, some part of IMD 16, or one of the leads or electrodes may be composed of a piezoelectric material that can generate current when excited mechanically by ultra sound waves transmitted from an external or implanted source.

In some examples, data generated by sensing module 114 or sensing module 118 and stored in memory 102 may be uploaded to a remote server, from which a clinician or another user may access the data to determine whether a potential sensing integrity issue exists. An example of a remote server includes the CareLink Network, available from Medtronic, Inc. of Minneapolis, Minn. An example system may include an external device, such as a server, and one or more computing devices that are coupled to IMD 16 and programmer 24 via a network.

In addition to the examples of FIGS. 1A, 1B, and 2 including cardiac therapy and neurostimulation therapy implemented in a single or separate devices, examples according to this disclosure also include a standalone INS device implanted within patient 12 and configured to function in a manner consistent with the description of neurostimulation therapy module 106 of IMD 16 or INS 26 shown in FIGS. 1A and 2, and 1B respectively.

Figure 3:
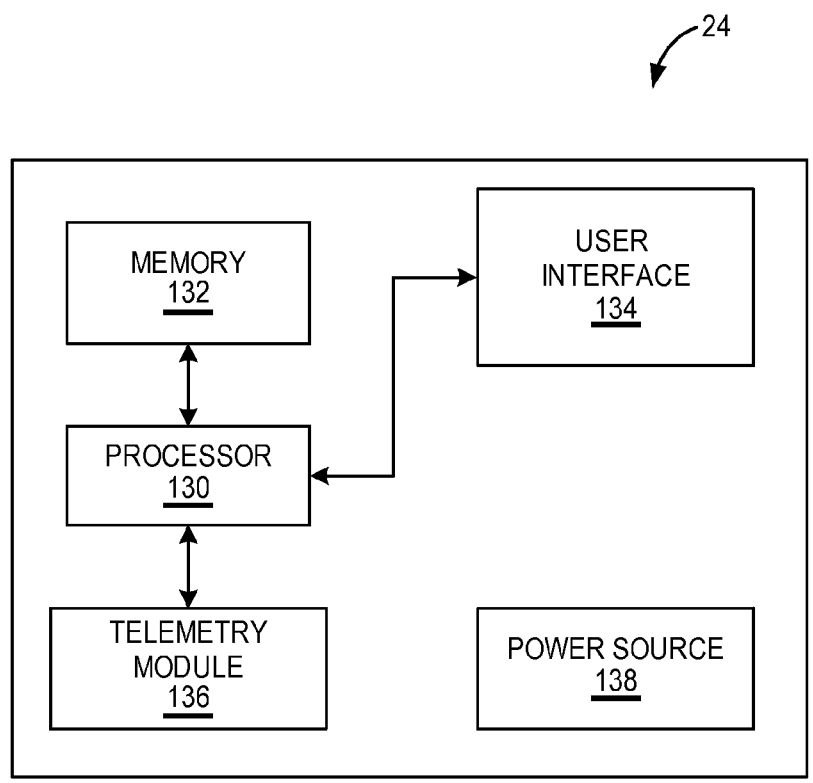
FIG. 3 is a functional block diagram of an example medical device programmer.

FIG. 3 is block diagram of example programmer 24 of FIGS. 1A and 1B. As shown in FIG. 3, programmer 24 includes processor 130, memory 132, user interface 134, telemetry module 136, and power source 138. Programmer 24 may be a dedicated hardware device with dedicated software for programming one or more of IMD 16, ICD 17, or INS 26. Alternatively, programmer 24 may be an off-the-shelf computing device running an application that enables programmer 24 to program one or more of IMD 16, ICD 17, or INS 26. For convenience and clarity, the description of FIG. 3 will be made with reference to the operation of programmer 24 with IMD 16. However, the components and functions of programmer 24 described herein are equally applicable to use with ICD 17, INS 26 or any other implantable medical device that may benefit from the functions provided by an external programming device such as programmer 24.

A user may use programmer 24 to select therapy programs (e.g., sets of stimulation parameters), generate new therapy programs, modify therapy programs through individual or global adjustments or transmit the new programs to IMD 16 (FIG. 1A). The therapy programs may be for either or both cardiac therapy module 104 and neurostimulation module 106 (FIG. 2). A clinician, e.g., may interact with programmer 24 via user interface 134, which may include a display to present a graphical user interface to a user, and a keypad or another mechanism for receiving input from a user.

Processor 130 can take the form of one or more microprocessors, DSPs, ASICs, FPGAs, programmable logic circuitry, or the like, and the functions attributed to processor 130 herein may be embodied as hardware, firmware, software or any combination thereof. Memory 132 may store instructions that cause processor 130 to provide the functionality ascribed to programmer 24 herein, and information used by processor 130 to provide the functionality ascribed to programmer 24 herein. Memory 132 may include any fixed or removable magnetic, optical, or electrical media, such as RAM, ROM, CD-ROM, hard or floppy magnetic disks, EEPROM, or the like. Memory 132 may also include a removable memory portion that may be used to provide memory updates or increases in memory capacities. A removable memory may also allow patient data to be easily transferred to another computing device, or to be removed before programmer 24 is used to program therapy for another patient. Memory 132 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 136, which may be coupled to an internal antenna or an external antenna. An external antenna that is coupled to programmer 24 may correspond to the programming head that may be placed proximate to the patient's body near the IMD 16 implant site, as described above with reference to FIG. 1A. Telemetry module 136 may be similar to telemetry module 108 of IMD 16 (FIG. 2).

Telemetry module 136 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 138 delivers operating power to the components of programmer 24. Power source 138 may include a battery and a power generation circuit to produce the operating power. In some examples, the battery may be rechargeable to allow extended operation of programmer 24.

Figure 4:
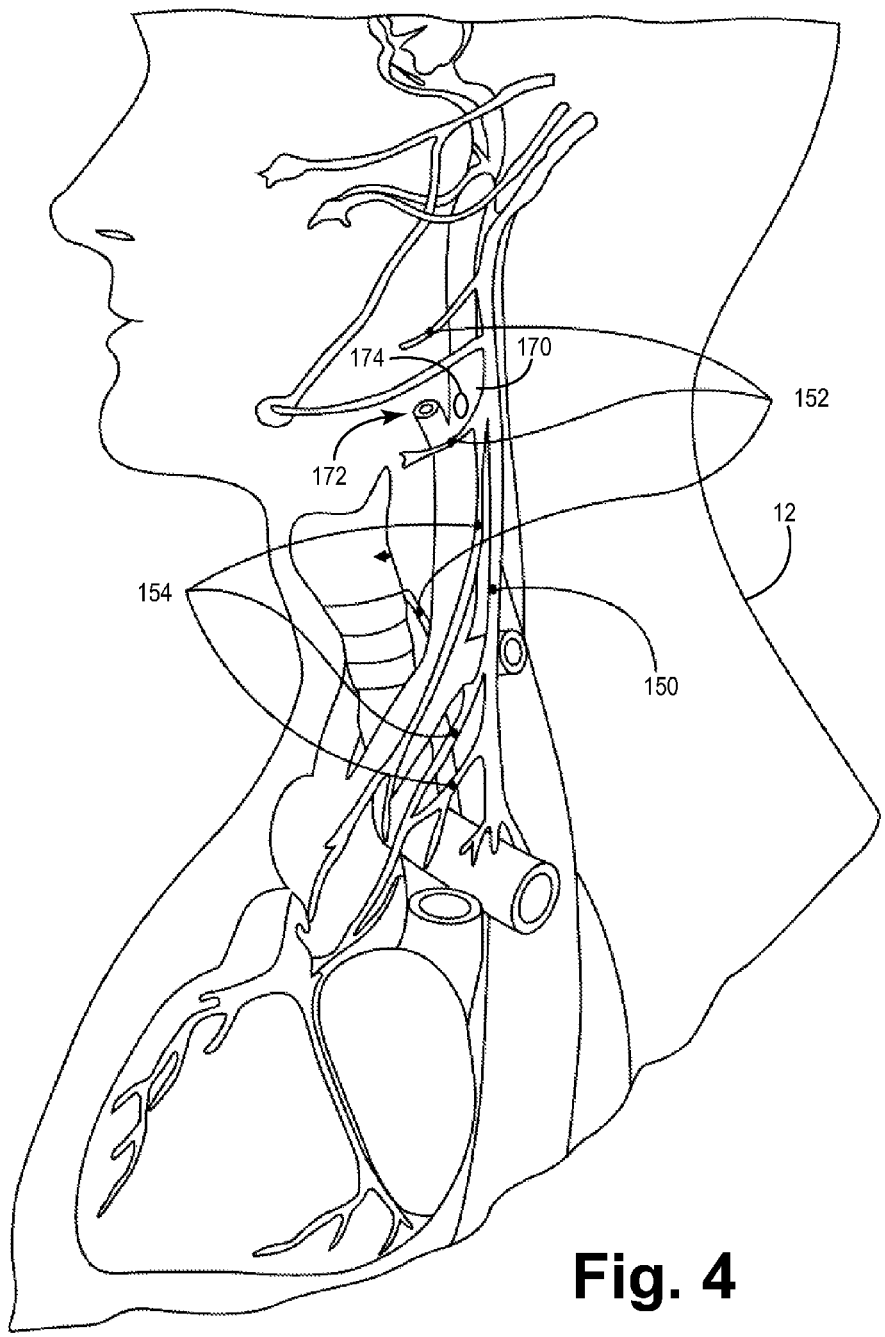
FIGS. 4 and 5 are schematic illustrations depicting relevant human anatomy for lead placement.
Figure 5:
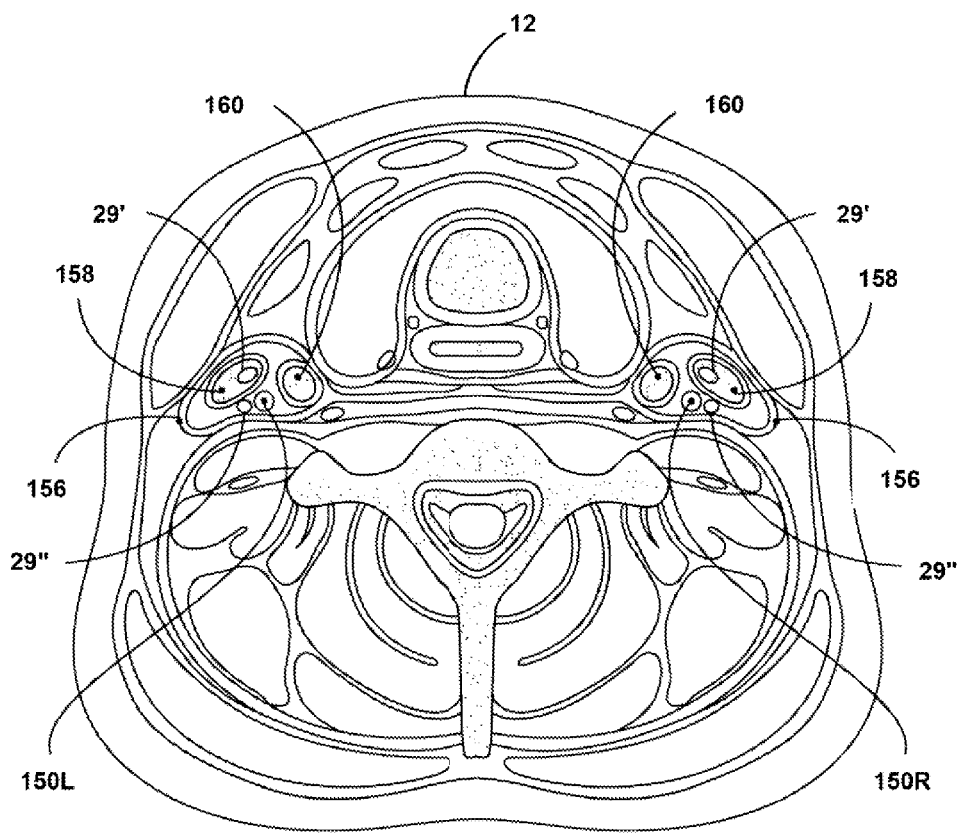

FIGS. 4 and 5 are schematic illustrations depicting relevant anatomy for VNS stimulation and/or stimulation of baroreceptors at carotid sinus. FIG. 4 illustrates vagus nerve 150 including many branches, such as pharyngeal and laryngeal branches 152, cardiac branches 154, as well as the gastric and pancreaticoduodenal branches (not specifically labeled in FIG. 4). The illustration of FIG. 5 is a cross section through the neck of patient 12 that shows carotid sheath 156 in which is contained internal jugular vein 158, carotid artery 160, and left and right vagus nerves 150L and 150R respectively. Vagus nerve 150 originates in the brainstem, runs in the neck through carotid sheath 156 with jugular vein 158 and common carotid artery 160, and then adjacent to the esophagus to the thoracic and abdominal viscera.

Vagus nerve 150 provides the primary parasympathetic nerve to the thoracic and most of the abdominal organs. For example, vagus nerve 150 provides parasympathetic innervation to the heart, and stimulation of the nerve has been demonstrated to drive the parasympathetic nervous system and thereby overcome an accelerated sympathetic tone, which may be exhibited by patients suffering from various tachycardia conditions, as well as heart failure. In one such tachycardia application, the efferent fibers of the vagus nerve, such as one or more superior and/or inferior cardiac branches may be electrically stimulated to manage the accelerated arrhythmia. Vagal nerve stimulation may also have afferent effects that result in nerve reflex changes that affect heart rate. In addition to heart innervations, vagus nerve 150 is responsible for such varied tasks as gastrointestinal peristalsis, sweating, as well as muscle movements related to speech. Electrical stimulation of vagus nerve 150 may be useful in treating, not only heart failure and arrhythmia conditions, but also various other conditions including, e.g., depression, epilepsy, and various gastrointestinal conditions. To determine the need for and/or response to nerve tissue stimulation according to methods and systems disclosed herein, ECG, heart rate, blood pressure, blood flow, cardiac output, and/or breathing, for instance, of patient 12 can be sensed. Such patient feedback information can be gleaned from, e.g., clinician observation, as well as employing one of implantable cardiac device (ICD) 17 shown in FIG. 1B or cardiac therapy module 104 shown in FIG. 2. Again, although the techniques disclosed herein are described generally in the context of stimulation of one of the vagus nerves on the vagal nerve trunk in the neck of a human patient, the methods and systems disclosed are also applicable to stimulation and treatment of other nerve tissues that are located in diverse locations including, e.g., baroreceptors, hypoglossal nerves, and nerve plexus and ganglia.

Electrical stimulation of baroreceptors of the carotid artery can also control certain physiological responses (e.g. blood pressure) of the body. The carotid artery is a major artery of the head and neck that helps supply blood to the brain. The carotid artery comprises an internal and external carotid artery 170, 172 respectively. Carotid sinus 174 contains numerous baroreceptors, which function as a "sampling area" for many homeostatic mechanisms for maintaining blood pressure. The carotid sinus baroreceptors are innervated by the sinus nerve of Hering, which is a branch of IX glossopharyngeal nerve (not shown). The glossopharyngeal nerve 178 synapses in the nucleus tractus solitarius (NTS) located in the medulla of the brainstem.

In addition to various biological structures of patient 12, FIG. 5 shows intra and extravascularly placed leads 29' and 29" respectively. Medical lead 29 is used for purposes of describing placement techniques according to this disclosure. In general, lead 29 may correspond to lead 28 shown in FIGS. 1A and 1B above. Intravascular lead 29' is arranged within internal jugular vein 158, while extravascular lead 29" is arranged within carotid sheath 156, adjacent vagus nerve 150. In addition to intra and extravascular leads 29' and 29" shown in FIG. 5, examples according to this disclosure include transvascular placement of lead 29 such that the lead passes from within a blood vessel of patient 12 through a wall of the vessel to terminate adjacent a target nerve tissue stimulation site. For example, lead 29 may be guided proximate a target site intravascularly through internal jugular vein 158 and then pierce a wall of jugular vein 158 to be arranged adjacent vagus nerve 150. Although the examples disclosed herein are generally described in the context of stimulating vagal nerves in the neck of patient 12, lead 29 and electrodes attached thereto may also be arranged for vagal nerve stimulation in, e.g., the thorax, and/or adjacent to the esophagus.

Extravascular lead placement techniques according to this disclosure provide placement of leads for nerve tissue stimulation and/or nerve signal sensing using implantation procedures with reduced invasiveness and without the need to anchor the leads at or very near their distal end. In general, the disclosed techniques include placing a portion of a medical lead having an electrode in an extravascular space within a sheath of tissue within a patient, and adjacent nerve tissue that is also within the sheath of tissue. The lead is anchored offset from the electrode at least partially outside of the sheath.

In one or more embodiments disclosed herein, the efficacy of the electrical stimulation delivered by electrode 228 to vagus nerve 150 may be compared to a threshold efficacy to determine whether or not therapy is satisfactorily achieving desired results with respect to achieving a lower heart rate. Efficacy refers, in general, to a combination of complete or partial alleviation of symptoms alone, or in combination with a degree of undesirable side effects. Efficacy may be measured, in general, by verbal feedback from patient 12, clinician observation of various conditions of patient 12, or sensory feedback from one or more devices including, e.g., ICD 17 shown in FIG. 1A or cardiac therapy module 104 shown in FIG. 4. Various physiological signals may be observed to measure the efficacy of the test stimulation, and thereby adjust the therapy. For example, to determine the response to stimulation of vagus nerve 150, ECG, heart rate, blood pressure, blood flow, cardiac output, and/or breathing, of patient 12 can be sensed or observed. These and other physiological signals may be detected in a variety of ways including sensing the signals using sense electrodes, pressure sensors, ultrasound sensors, motion sensors or other devices. In other examples, physiological reactions of patient 12 may be observed or measured by, e.g., a clinician. In one example, efficacy may be measured by a sensor including, e.g., an accelerometer that determines if stimulation of the neck muscles or phrenic nerve of patient 12 is occurring with or instead of stimulation of vagus nerve 150. In another example, a pressure sensor arranged coincident with or connected to lead 29 may measure blood pressure by detecting the pressure within jugular vein 158. A pressure sensor, or other type of physiological feedback sensor, may also, in some examples, be connected to catheter 220 to measure, e.g., blood pressure within vein 158.

In the event the nerve tissue stimulation meets or exceeds the threshold efficacy, lead 29 and electrode 228 may be chronically deployed within jugular vein 158 adjacent vagus nerve 150. On the other hand, if the nerve stimulation delivered by electrode 228 does not provide the threshold level of efficacy in relieving the symptoms of patient 12, catheter 220 and electrode 228 may be repositioned within jugular vein 158 to improve the location of the components, in particular electrode 228 with respect to vagus nerve 150.

In the event the nerve tissue stimulation meets or exceeds the threshold efficacy, lead 29 and electrode 228 may be chronically deployed by advancing the lead from the tip of catheter 220 within jugular vein 158 toward vagus nerve 150. On the other hand, if the nerve stimulation delivered by electrode 229 does not provide the threshold level of efficacy in relieving the symptoms of patient 12, the therapy can be adjusted. After repositioning catheter 220 and electrode 229, the process of stimulating vagus nerve 150 and comparing the efficacy of the nerve stimulation to a threshold efficacy may be repeated until the arrangement of catheter 220 with respect to vagus nerve 150 delivers electrical stimulation therapy that meets or exceeds the threshold efficacy level.

In practice, lead 29, electrode 228, and fixation member 274 may be advanced laterally from the tip of catheter 220 toward the wall of jugular vein 158 adjacent vagus nerve 150. In some examples, lead 29 may be directed toward the wall of vein 158 along a trajectory that is approximately perpendicular to the wall. Active fixation member 274 engages the wall of the lumen of jugular vein 158 by, e.g., twisting lead 29 to screw the helical fixation member into the wall. After actively fixing lead 29 and electrode 228 to the wall of vein 158 adjacent vagus nerve 150, catheter 220 may be removed, after which lead 29 and electrode 228 will lay down along and approximately tangential to the wall of vein 158.

In some examples, active fixation member 274 may be electrically active such that it acts as an electrode in addition to or in lieu of electrode 228. Fixation member 274 may have a variety of lengths and helical pitches. In some examples, fixation member 274 may have a length in the range from and including approximately 0.5 millimeters to and including approximately 2.5 millimeters. In other examples, fixation member 274 may have a length in the range from and including approximately 1 millimeters to and including approximately 2 millimeters. The pitch of the helical coil of active fixation member 274 may also vary in different examples according to this disclosure. In general, in examples in which fixation member 274 is electrically active, it may be desirable to increase the pitch to increase the amount of surface area engaging tissue of the wall of jugular vein 158. In some examples, fixation member 274 may have a helical pitch in the range from and including approximately 0.5842 millimeters to and including approximately 1.016 millimeters.

In some examples, a cylindrical lead member may include an electrical stimulator and, in some cases, need not be coupled to an implantable medical device via a lead. In such examples, the electrical stimulator on, within or attached to the cylindrical lead member may be powered by radio frequency pulses delivered from either an external or a subcutaneously implanted RF transmitter to a receiver unit arranged with the stimulator or cylindrical lead member. In other examples, some part of the stimulator or cylindrical lead member may be composed of a piezoelectric material that can generate current when excited mechanically by ultra sound waves transmitted from an external or implanted source.

Similar to intravascular techniques, transvascular lead placement proximate a target nerve tissue site generally requires minimally invasive surgical techniques because the leads are guided to the site through a blood vessel, e.g., a vein or artery that may be readily accessible, e.g., transcutaneously through a small incision. Unlike intravascular, however, transvascular techniques guide the lead adjacent the target tissue site and then pierce the vessel wall to arrange the lead and electrodes outside of the vessel adjacent the nerve tissue at which therapy is directed. Transvascular lead placement techniques according to this disclosure provide for lead placement relative to the target nerve tissue and neighboring blood vessels to improve the therapeutic effects of electrical stimulation provided to the patient by lead electrodes. Implantable electrical stimulation systems and methods in accordance with this disclosure may be used to deliver therapy to patients suffering from conditions that range from chronic pain, tremor, Parkinson's disease, and epilepsy, to urinary or fecal incontinence, sexual dysfunction, obesity, spasticity, hypertension, heart failure and gastroparesis. Specific types of electrical stimulation therapies for treating such conditions include, e.g., cardiac pacing, neurostimulation, muscle stimulation, or the like.

Figure 6:
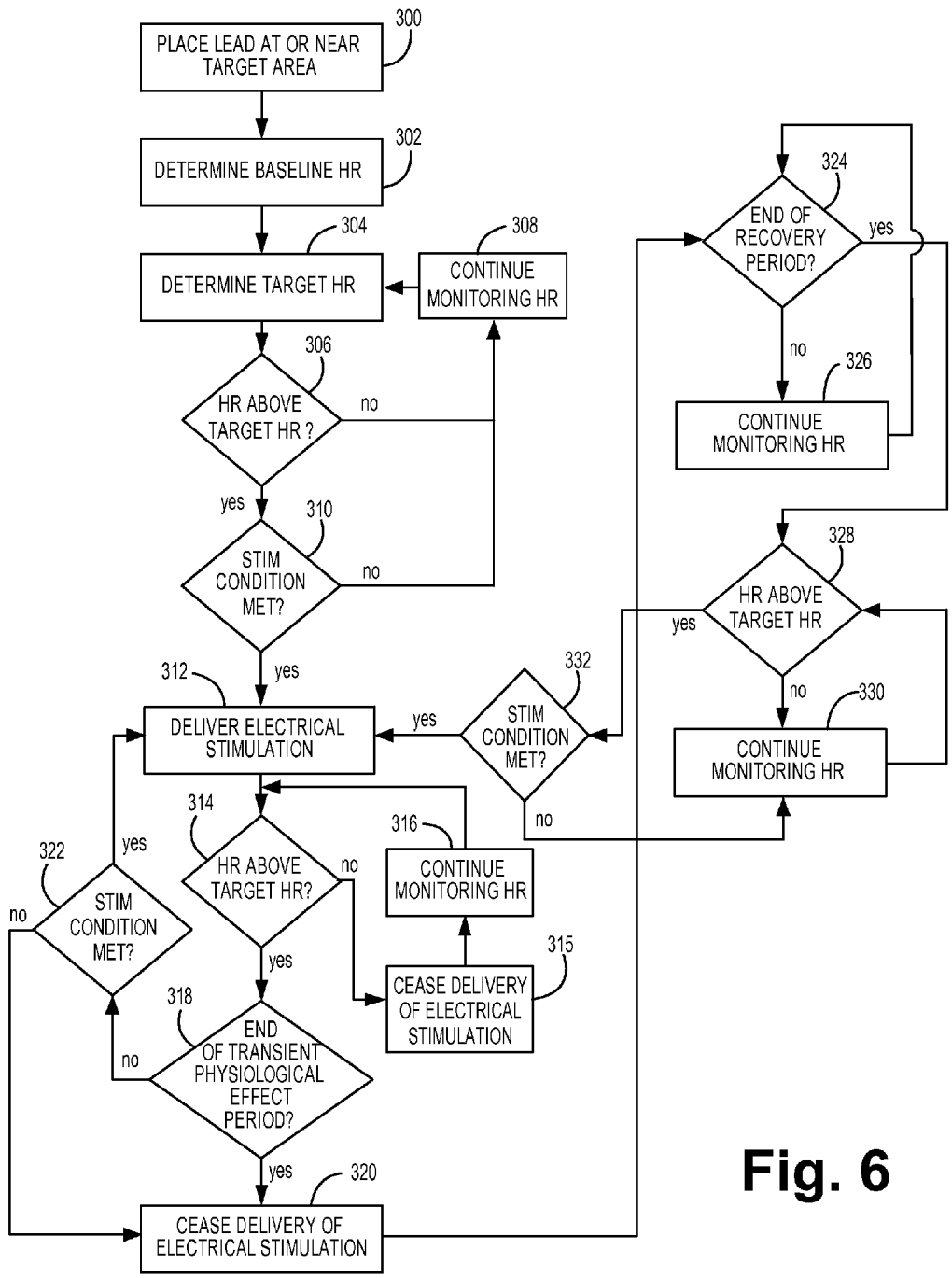
FIG. 6 is a flow diagram for delivering electrical stimulation in synchronization with transient effects.

FIG. 6 depicts an exemplary method for delivering electrical stimulation to nerve tissue (e.g. vagal nerve tissue) in synchronization with transient physiological effects in a patient. At block 300, electrodes on lead 18, 20, and/or 22, placed at or near a target area, can be used to sense heart beats from heart 14 while processor 100 determines a baseline heart rate at block 302 while the patient is at rest. Generally, many methods can be used to determine heart rate, including through acoustic sensors, an accelerometer on an indwelling lead in a ventricle, impedance measurements of the blood volume in the heart or a chamber thereof, electrocardiographic analysis based on peak to peak amplitude measurements and the like, all generally well known and based on a periodically oscillating signal value, the periodicity of which indicates the rate. For example, when an R-wave passes as indicated by a cardiac electrogram measurement of the passing of a peak amplitude signal, until the next R wave of similar amplitude height, a time measurement is made. This is the R-R interval value. An interval value is the inverse of heart rate. (Thus an R-R interval of 1000 milliseconds is 60 beats per minute). There are many variations on how to determine HR and they are well known, and any of these of reasonable accuracy can be used for the purposes of the invention herein. For a simple particular method, a count of time units or clock cycles per R-wave signal in an input electrocardiogram signal stream may be monitored and a value computed based on this measure and stored in memory by a processor. The R-waves themselves may be found in variation in electrocardiogram amplitude signals by finding the peaks or level crossing detection or in many other ways currently known. At the time of the storing of an HR value for the HR variable for a given time period comprised of a number of clock cycles/time units, a value is stored for the level of patient activity. These two values (HR and "activity" or cardiac demand) can be combined in a combination routine or through an analog process if desired or they may be stored independently, preferably in a memory as digital values, for later retrieval and manipulation by a program in an external device if desired. In any event, the combination of HR and/or activity value for each time can be stored somewhere to display a plot of heart rate activity coefficient (HRAC) over time, or to provide any other useful application of this set of data values. Detailed examples of determining a heart rate may be seen with respect to U.S. Pat. No. 6,529,771 issued to Kieval et al on Mar. 4, 2003, and assigned to the assignee of the present invention, the disclosure of which is incorporated by reference in its entirety herein.

Once the baseline heart rate is established, a desirable target heart rate is set for the patient at block 304. A target heart rate is lower than the baseline heart rate. For example, the target heart rate maybe a couple of heart beats per minute (i.e. two, three or four heart beats per minute) lower than the baseline heart rate. Patients afflicted with congestive heart failure typically can benefit by having a lower heart rate even if the lower heart rate may not be an ideal rate for a healthy person.

After the baseline heart rate and the target heart rate are established, a patient's heart beat can be continuously sampled to determine a heart rate that can be compared to the baseline heart rate. If the heart rate is not above or equal to the target heart rate, the processor 100 continues to monitor the patient's heart rate at block 308 and then again compares the heart rate (referred to as a first heart rate) to the target heart rate at block 306. A high heart rate is a heart rate that is equal to or greater than the target heart rate. If the heart rate is not above the target heart rate, the NO path is followed to block 308 to continue monitoring the patient's heart rate. If the heart rate is above the target heart rate, the YES path can be followed to block 310.

At block 310, a determination is made as to whether electrical stimulation should be delivered to a patient. A wide variety of conditions can satisfy the delivery of stimulation condition at block 310. For example, a patient's heart may require pacing or defibrillation shocks. Conditions for delivering pacing pulses and/or defibrillation shocks are embodied in the computer instructions stored in memory 102 and accessed by the processor 100 from memory 102. The computer instructions executed by the processor 100 may be customized to a patient to deliver electrical stimulation when particular conditions are met and/or when general conditions are met. If a stimulation condition is not met, a NO path is followed to block 308 to continue monitoring a patient's heart rate. If the stimulation condition is met, the YES path is followed and electrical stimulation is delivered to the patient at block 312. Electrical stimulation is initiated (block 312) from the IMD 16 to an electrode at a distal end of the lead 28, which is located proximate vagal nerve tissue of the patient. For example, the electrode at a distal end of the lead 28 can be located on the vagus nerve proximal to the target organ. Specifically, for heart rate, the electrode at a distal end of the lead can be located on the vagus nerve proximal to the heart. After electrical stimulation has begun, the patient's heart rate (referred to as a second heart rate) is compared to the target heart rate at block 314. If the patient's heart rate is below the target heart rate, the NO path ceases electrical stimulation at block 315, the patient's heart rate is continuously monitored at block 316. The patient's heart rate is then compared to the target heart rate at block 314. Alternatively, If the patient's heart rate is equal to or greater than the target heart rate, the YES path allows a determination to be made as to whether the end of a transient physiological effect period has occurred at block 318. For purposes of the specification and the claims, transient physiological effect period is a period of time during which stimulation has an increased level of efficacy.

The transient physiological effect period is a short time period such as 5 seconds from the time in which stimulation is initiated and a patient's heart rate is detected at the lower heart rate. It is believed that the patient's body undergoes a period of accommodation or habituation in which the body begins to adapt to electrical stimulation such that the electrical stimulation has a diminishing effect on the patient's heart rate. The NO path as to whether the end of the transient physiological effect period has occurred transfers control to block 322. At block 322, a determination is made as to whether another stimulation condition has been met at block 322. If a stimulation condition is met, the YES path initiates electrical stimulation at block 312. In contrast, if a stimulation condition is not met, the NO path ceases electrical stimulation at block 320.

The YES path as to whether the end of the transient physiological effect period has occurred transfers control to block 320. As previously stated, block 320 ceases delivery of electrical stimulation to the vagus nerve.

After electrical stimulation has been stopped at block 320, a determination is then made as to whether a recovery period has ended at block 324. A recovery period is a period of time when the body is attempting to regain or return to a normal state. A normal state is when a body such as tissue is able to respond to electrical stimulation. During the recovery period, additional electrical stimulation does not provide a beneficial physiological effect to the patient. A recovery period ends when a body or tissue is no longer refractory or is no longer unresponsive to the effect of electrical stimulation. For example, a recovery period ends when a body or tissue is able to be activated and/or respond to electrical stimulation. After the recovery period, electrical stimulation has an increased level of efficacy.

The recovery period can be determined in numerous ways. For example, the recovery period could be determined for each individual patient by the IMD 16 periodically sending test electrical stimuli to the nerve tissue to determine whether the heart rate can be lowered at any level. If there is no effective response (i.e. lower heart rate), the recovery period has not yet ended. Another way to define the recovery period is to predetermine an average time for a refractory period for heart failure patients in general or customized to a specific patient. The average recovery time could then be stored in the memory 102 of the IMD 16 and used in the computer instructions to ensure electrical stimulation is not delivered to the nerve tissue until the recovery period is over. If the recovery period has not yet ended, the NO path allows the patient's heart rate to be continuously monitored at block 326 and the end of the recovery period is again checked at block 324.

If the recovery period has ended, the YES path another determination is made at block 328 as to whether the heart rate (referred to as a third heart rate) is above the target heart rate. If the heart rate is above or equal the target heart rate, stimulation condition at block 332 is checked. If the processor 100 determines that a stimulation condition exists, the YES path causes electrical stimulation to be delivered to the vagus nerve at block 312. The NO path from block 332 allows the patient's heart rate to be monitored at block 330. The blocks are repeatedly performed unless a termination condition is met indicating therapy is no longer needed. Exemplary termination conditions include the heart returns to the desired heart rate on its own, the patient begins to exercise as detected by the device such as the microprocessor 100 executing computer instructions in the IMD 16 and it is no longer desirable to suppress the heart rate or hemodynamic parameters such as blood pressure are too low.

Figure 7:
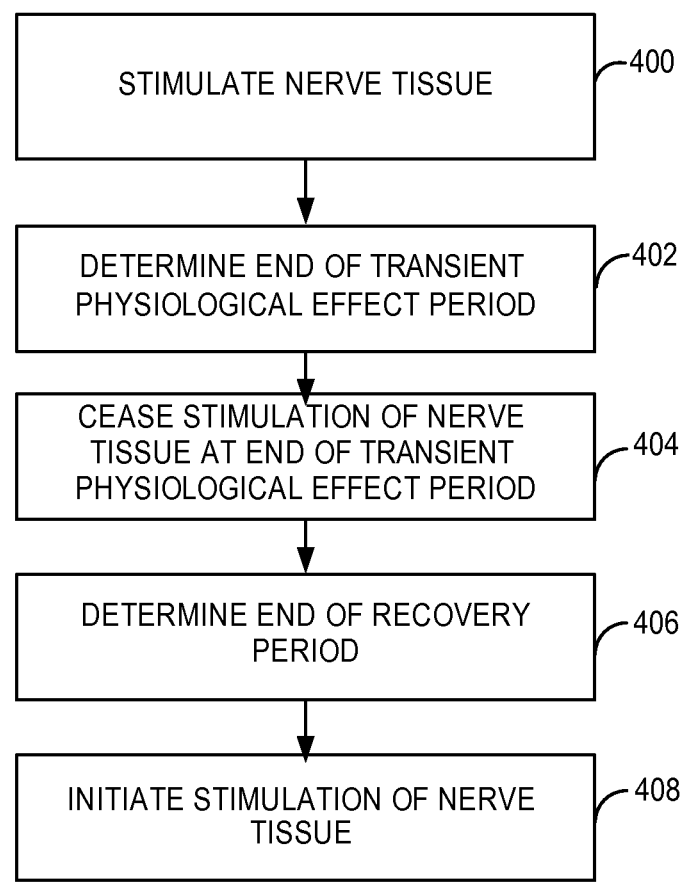
FIG. 7 is a flow diagram for delivering electrical stimulation to nerve tissue in synchronization with transient effects.

FIG. 7 is a flow diagram for delivering electrical stimulation to nerve tissue in synchronization with transient effects. At block 400, a medical electrical lead is placed proximate targeted nerve tissue. At block 402, an end to the transient physiological effect period is determined. At block 404, stimulation of nerve tissue is terminated at the end of transient physiological effect period. At block 406, an end to a recovery period is determined. At block 408, electrical stimulation of nerve tissue is again initiated.

Figure 8:
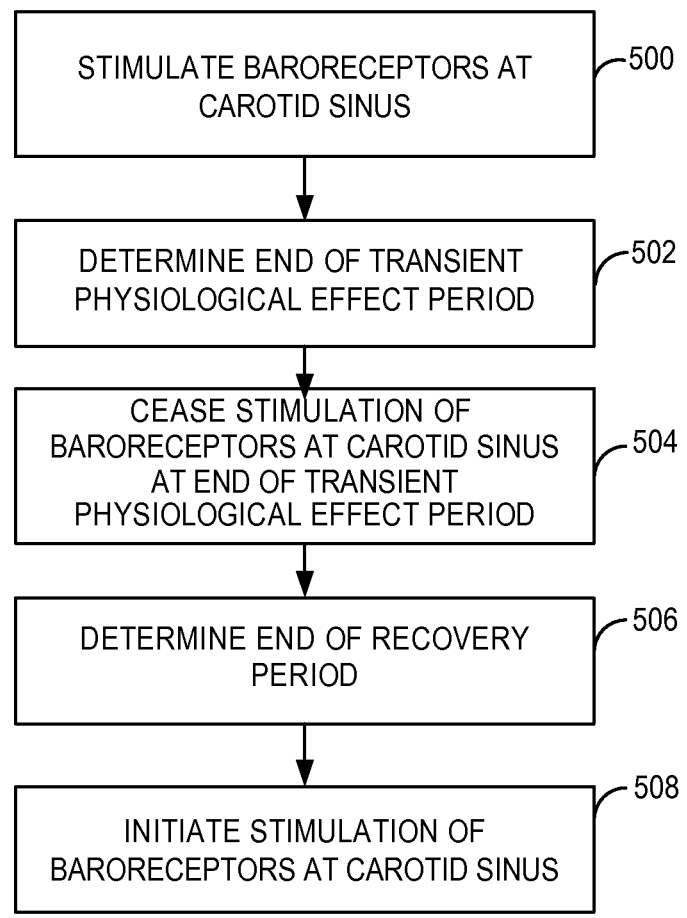
FIG. 8 is a flow diagram for delivering electrical stimulation to baroreceptors at carotid sinus in synchronization with transient effects.

FIG. 8 is a flow diagram for delivering electrical stimulation to baroreceptors at carotid sinus in synchronization with transient effects. At block 500, a medical electrical lead is placed proximate targeted nerve tissue. At block 502, an end to the transient physiological effect period is determined. At block 504, stimulation of nerve tissue is terminated at the end of transient physiological effect period. At block 506, an end to a recovery period is determined. At block 508, electrical stimulation of baroreceptors at carotid sinus is again initiated.

Various examples have been described in this disclosure. These and other examples are within the scope of the following claims. In one or more other embodiments, baroreceptor (or baroceptors) stimulation could be used to reduce blood pressure. All the same descriptions relative to FIG. 6, could apply here except the electrical stimulation is applied to the baroreceptors at the carotid sinus and the major physiologic parameter to follow would be blood pressure. Baroreceptors are sensors located in the blood vessels. Baroreceptors, mechanoreceptors, can detect amount of stretch of the blood vessel walls which directly relates to blood pressure as the blood flows therethrough. In response to the detected stretch of the blood vessel walls, baroreceptors send a signal to the nervous system. The nucleus tractus solitarius in the medulla oblongata recognizes changes in the firing rate of action potentials from the baroreceptors, and influences cardiac output and systemic vascular resistance through changes in the autonomic nervous system.

In still yet another embodiment, sympathetic tone (e.g. parasympathetic) can be used to determine if sufficient vagal stimulation has occurred. For example, sympathetic tone could be used to switch on or off electrical stimulation delivered to the vagal nerve.

In still yet another embodiment, heart rate variability could be used to switch on or off electrical stimulation delivered to the vagal nerve.

In one or more embodiments, it will be appreciated that while one or more embodiments are described as having a physiological condition higher than a target physiological condition to trigger electrical stimulation of tissue, in one or more other embodiments, a physiological response can be lower than a target physiological response, which can cause initiation of electrical stimulation of tissue.

The invention claimed is:

1. A method of using an implantable medical device comprising:
    delivering electrical stimulation proximate nerve tissue of a patient during a transient physiological effect period separated by a recovery period, the transient physiological effect period is when electrical stimulation has an increased level of efficacy and the recovery period is when additional electrical stimulation does not provide a beneficial physiological effect to the patient; and
    determining an end of the recovery period by sending test electrical stimuli to the nerve tissue and monitoring for an effective response to the test electrical stimuli.

2. The method of claim 1 wherein the transient physiological effect period ends when a physiological condition indicates habituation to the electrical stimulation.

3. The method of claim 1 wherein the transient physiological effect period is less than or about equal to 5 seconds from a time in which a physiological condition is lower than a target physiological condition.

4. The method of claim 1 wherein after the recovery period, electrical stimulation has an increased level of efficacy.

5. The method of claim 1 further comprising:
    determining a baseline physiological condition; and
    determining a target physiological condition in response to determining the baseline physiological condition.

6. The method of claim 5 further comprising:
    determining a first physiological condition is higher than a target physiological condition.

7. The method of claim 6 further comprising:
    determining a second physiological condition is higher than the target physiological condition.

8. The method of claim 7 wherein the first physiological condition relates to one of a blood pressure, a heart rate, heart rate variability, and a sympathetic tone.

9. The method of claim 7 wherein the second physiological condition relates to one of a blood pressure, a heart rate, heart rate variability, and a sympathetic tone.

10. The method of claim 1 wherein the nerve tissue is a vagal nerve.

11. A method of using an implantable medical device comprising:
    delivering electrical stimulation proximate nerve tissue of a patient;
    determining a first physiological condition is higher than a target physiological condition;
    determining an end to a transient physiological effect period;
    ceasing electrical stimulation in response to determining the end of the transient physiological effect period;
    determining an end of a recovery period by sending test electrical stimuli to the nerve tissue and monitoring for an effective response to the test electrical stimuli;
    determining a second physiological condition is higher than the target physiological condition; and
    delivering automatically electrical stimulation proximate the nerve tissue in response to determining a second physiological condition is greater than the target physiological condition.

12. The method of claim 11 wherein the transient physiological effect period is less than or equal to 5 seconds from a time in which a patient's physiological condition is better than the target physiological condition.

13. The method of claim 11 wherein the transient physiological effect period ends when a physiological condition indicates accommodation to the electrical stimulation.

14. The method of claim 11 wherein the first physiological condition relates to one of a blood pressure, a heart rate, heart rate variability, and a sympathetic tone.

15. The method of claim 11 wherein the second physiological condition relates to one of a blood pressure, a heart rate, heart rate variability, and a sympathetic tone.

16. A method of using an implantable medical device comprising:
    determining a baseline heart rate;
    determining a target heart rate;
    determining a first heart rate is equal to or greater than the target heart rate;
    initiating electrical stimulation proximate vagal nerve tissue of the patient, in response to determining the first heart rate is equal to or greater than the target heart rate;
    determining a second heart rate is equal to or greater than the target heart in response to initiating electrical stimulation proximate vagal nerve tissue;
    determining an end to a transient physiological effect period in response to determining the second heart rate;
    ceasing electrical stimulation in response to determining the end of the transient physiological effect period;
    determining an end of a recovery period in response to ceasing delivery of the electrical stimulation by sending test electrical stimuli during the recovery period to the nerve tissue and monitoring for an effective response to the test electrical stimuli;

determining a third heart rate is equal to or greater than the target heart rate in response to determining the end of the recovery period; and delivering automatically electrical stimulation proximate vagal nerve tissue of the patient, in response to determining a third heart rate is equal to or greater than the target heart rate.

17. The method of claim 16 wherein the transient physiological effect period is less than or equal to 5 seconds from a time in which a patient's heart rate is detected at a heart rate lower than the target heart rate.

18. The method of claim 16 wherein the transient physiological effect period ends when a heart rate indicates accommodation to the electrical stimulation.

19. A method of using an implantable medical device comprising:
determining a first heart rate in a patient;
delivering electrical stimulation proximate vagal nerve tissue of the patient until a predetermined second heart rate is attained during a transient effect period, the second heart rate is lower than the first heart rate;
ceasing electrical stimulation in response to determining a second heart rate;
determining an end of the recovery period by sending test electrical stimuli to the vagal nerve tissue and monitoring for an effective response to the test electrical stimuli;
determining the heart rate starting to return to or completely returning to the first heart rate after determining the end of the recovery period;
delivering automatically electrical stimulation proximate vagal nerve tissue of the patient after the recovery period has ended; and
lowering the heart rate to the second heart rate.

20. The method of claim 19 further comprising determining an efficacy of the nerve tissue stimulation.

21. A method of obtaining a target heart rate through use of an implantable medical device comprising:
delivering electrical stimulation proximate vagal nerve tissue of a patient during a transient physiological effect period separated by a recovery period, the transient physiological effect period is when electrical stimulation has an increased level of efficacy and the recovery period is when additional electrical stimulation does not provide a beneficial physiological effect to the patient; and
determining an end of the recovery period by sending test electrical stimuli to the nerve tissue and monitoring for an effective response to the test electrical stimuli.

22. A method of using an implantable medical device comprising:
automatically delivering electrical stimulation proximate nerve tissue of a patient during a transient physiological effect period separated by a recovery period, the transient physiological effect period is when electrical stimulation has an increased level of efficacy in achieving a target physiological condition and the recovery period is when additional electrical stimulation does not provide a beneficial effect toward achieving the target physiological condition;
determining during the transient physiological effect period and subsequent to achieving the beneficial effect if the target physiological condition is not met;
ceasing the electrical stimulation in response to determining the target physiological condition is not met;
determining an end of the recovery period by sending test electrical stimuli to the nerve tissue and monitoring for an effective response to the test electrical stimuli;
determining if the target physiological condition is not met subsequent to determining the end of the recovery period; and
delivering automatically electrical stimulation proximate the nerve tissue in response to determining the target physiological condition is not met subsequent to determining the end of the recovery period.

* * * * *